United States Patent
Shi et al.

(10) Patent No.: US 11,853,038 B1
(45) Date of Patent: Dec. 26, 2023

(54) OPTIMAL CONTROL METHOD OF POLLUTANT FLUX INTO COASTAL WATERS BASED ON VIRTUAL DISCHARGE AMOUNT

(71) Applicant: FIRST INSTITUTE OF OCEANOGRAPHY, MINISTRY OF NATURAL RESOURCES, Qingdao (CN)

(72) Inventors: Honghua Shi, Qingdao (CN); Wei Zheng, Qingdao (CN); Yongzhi Wang, Qingdao (CN); Pei Huang, Qingdao (CN)

(73) Assignee: FIRST INSTITUTE OF OCEANOGRAPHY, MINISTRY OF NATURAL RESOURCES, Qingdao (CN)

( * ) Notice: Subject to any disclaimer, the term of this patent is extended or adjusted under 35 U.S.C. 154(b) by 0 days.

(21) Appl. No.: 18/312,693

(22) Filed: May 5, 2023

(30) Foreign Application Priority Data

Dec. 15, 2022 (CN) .......................... 202211609077.X

(51) Int. Cl.
G05B 19/416 (2006.01)
(52) U.S. Cl.
CPC .. G05B 19/416 (2013.01); *G05B 2219/37371* (2013.01)
(58) Field of Classification Search
CPC .................. G05B 19/416; G05B 2219/37371
See application file for complete search history.

(56) References Cited

U.S. PATENT DOCUMENTS

2022/0358266 A1* 11/2022 Li ..................... G06F 18/23213

FOREIGN PATENT DOCUMENTS

| CN | 105260790 A | 1/2016 |
| CN | 105320828 A | 2/2016 |
| WO | 2021208393 A | 10/2021 |

OTHER PUBLICATIONS

Gorelick, Steven M. "A model for managing sources of groundwater pollution." Water Resources Research 18.4 (1982): 773-781. (Year: 1982).*

(Continued)

*Primary Examiner* — Christopher E. Everett
(74) *Attorney, Agent, or Firm* — Kaplan Breyer Schwarz, LLP; Stuart H. Mayer

(57) ABSTRACT

Disclosed is an optimal control method of pollutant flux into the coastal waters based on virtual discharge amount, comprising: setting water quality control points and water quality control objectives in target sea areas; constructing response matrix of coastal water quality to pollution source discharged from land, and extracting response coefficient matrix of different pollution sources and different control points for the water quality control points through the response coefficient matrix of coastal water quality to pollution source discharged from land; and establishing a control model for total discharge amount of pollutants into the coastal waters through the response coefficient matrix; and calculating an optimal control amount of flux of the different pollution sources into the coastal waters based on the control model for total discharge amount of pollutants into the coastal waters.

4 Claims, 1 Drawing Sheet

(56) References Cited

OTHER PUBLICATIONS

Djuwita, Mitta Ratna, et al. "Pollution Load Allocation on Water Pollution Control in the Citarum River." Journal of Engineering & Technological Sciences 53.1 (2021). (Year: 2021).*

Babamiri, O., Marofi, S. A multi-objective simulation-optimization approach for water resource planning of reservoir-river systems based on a coupled quantity-quality model. Environ Earth Sci 80, 389 (2021). (Year: 2021).*

Xue-qing Zhang, "study on the environmental capacity in Jiaozhou Bay" Marin Environmental Science, vol. 26, No. 4, Aug. 2007.

* cited by examiner

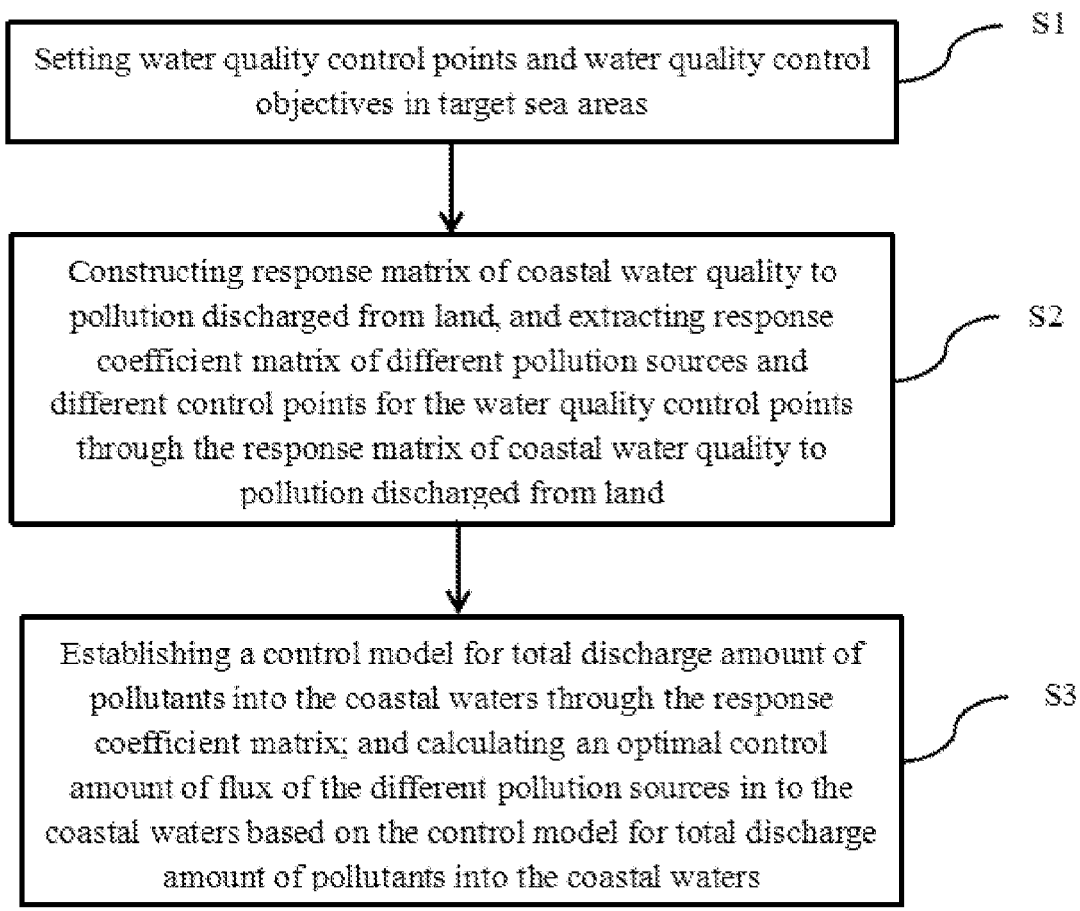

OPTIMAL CONTROL METHOD OF POLLUTANT FLUX INTO COASTAL WATERS BASED ON VIRTUAL DISCHARGE AMOUNT

CROSS-REFERENCE TO RELATED APPLICATIONS

This application claims priority to Chinese Patent Application No. 202211609077.X, filed on Dec. 15, 2022, the contents of which are hereby incorporated by reference.

TECHNICAL FIELD

The application relates to the technical field of marine environmental protection, and in particular to an optimal control method of pollutant flux into coastal waters based on virtual discharge amount.

BACKGROUND

The population and industry in coastal areas are relatively concentrated, and the pollutants produced by the industrial production and human life flow into the coastal waters by rivers or sewage outlets, improving the risk of eutrophication in the coastal waters. Moreover, it is easy to cause coastal ecosystem degradation if the pollutants are discharged excessively or improperly. Pollution discharged from land is one of the main causes of ecosystem degradation in some coastal waters, and it is important to reduce or optimize the pollutant flux into the coastal waters to maintain the coastal ecosystem health. However, due to considerable discharge points, great spatial differences in diffusion capacity of the sea, and diversified requirements for industrial production and living security in river basins, it is very difficult to optimize the discharge reduction scheme of pollutants discharged from land flowing into the coastal waters, and it is urgent to design a set of simple, relatively unified and easy-to-calculate optimization method for the discharge reduction scheme of total pollutants flowing into the coastal waters.

SUMMARY

The objective of the present application is to provide an optimal control method of pollutant flux into coastal waters based on virtual discharge amount to solve the problems in the prior art.

In order to achieve the above objectives, the present application provides the following scheme.

An optimal control method of pollutant flux into coastal waters based on virtual discharge amount includes:
  setting water quality control points and objectives in target sea areas;
  constructing response coefficient fields of pollution sources discharged from land and coastal water quality, and extracting the response coefficient matrix of different pollution sources and different control points for the water quality control points through the response coefficient matrix of coastal water quality to pollution discharged from the land;
  establishing a control model for the total discharge amount of pollutants into the coastal waters through the response coefficient matrix, and calculating an optimal control amount of flux of the different pollution sources into the coastal waters based on the control model for the total discharge amount of pollutants into the coastal waters.

Optionally, principles of setting the water quality control points in the target sea areas include completeness, comparability of data and finiteness, where the completeness means that selected control points cover marine functional zone types contained in all water quality control sea areas, and control point stations are evenly distributed, the comparability of data means stations with rich historical investigation data are preferably selected to be used for comparative research, and the finiteness is to consider representativeness of the stations, expense of monitoring and investigation and a computation amount of the control model at the same time.

Optionally, the basis for setting the water quality control objectives is the application types of the sea areas where the water quality control points are located.

Optionally, the application types of the sea areas include:
  a water quality control objective of sea areas in marine fishery waters, marine nature reserves and endangered marine life reserves;
  a water quality control objective of sea areas in aquaculture areas, bathing beaches, marine sports or entertainment areas where human bodies are in direct contact with seawater, and industrial water areas directly related to human consumption;
  a water quality control objective of sea areas in industrial water consumption areas and coastal scenic tourist areas;
  a water quality control objective of sea areas in marine port waters and marine development operation areas.

Optionally, constructing the response matrix of coastal water quality to pollution discharged from land includes:
  calculating steady-state concentration fields formed by individual discharge of each pollution factor of each pollution source item under unit intensity respectively based on the relationship between pollution sources discharged from land and coastal water quality response concentration, and establishing a two-dimensional water quality model of the target sea areas based on pollution source positions and the water quality control points;
  simulating and studying effects of the different pollution sources discharged into the coastal waters on the water quality of the sea areas based on the two-dimensional water quality model of the target sea areas, and obtaining the response matrix of coastal water quality to pollution discharged from land corresponding to the different pollution sources.

Optionally, parameters of the response matrix of coastal water quality to pollution discharged from land include:
  convective diffusion coefficients and boundary conditions, where the convective diffusion coefficients include a diffusion coefficient, an attenuation coefficient and an initial concentration, and the boundary conditions include open boundary conditions, inflow, outflow and shore boundary conditions.

Optionally, establishing the control model for total discharge amount of pollutants into the coastal waters includes:
  Under the premise that the sum of the actual pollutant concentrations at all water quality control points does not exceed the sum of their target concentrations, and the proportion of water quality exceeding the standard at each control point does not exceed the water quality regulation coefficient at that point, with the goal of maximizing the virtual total discharge amount in the sea areas, the total discharge amount control model of the pollutants is constructed by solving the optimal solution of the objective planning model.

Optionally, an objective function of the control model for the total discharge amount of pollutants into the coastal waters is:

$$\max Q = \sum_{j=1}^{n} \lambda_j Q_j,$$

where $Q_j$ is load of a j-th pollution source into the coastal waters, $\lambda_j(\lambda_j \geq 1)$ is the regulation coefficient of the j-th pollution source, Q is the virtual total discharge amount and n is the quantity of pollution sources discharged from land into the coastal waters.

Optionally, constraints of the control model for the total discharge amount of pollutants into the coastal waters include:

$$\begin{cases} \sum_{i=1}^{m}\left(C_i^0 + \sum_{j=1}^{n}\alpha_{ij}Q_j\right) \leq \sum_{i=1}^{m}C_i^s \\ C_i^0 + \sum_{j=1}^{n}\alpha_{ij}Q_j \leq (1+r_i)C_i^s, i = 1, 2, \ldots, m, \\ Q_j \geq Q_{min}^0 \geq 0, j = 1, 2, \ldots n \end{cases}$$

where n is the quantity of pollution sources discharged from land into the coastal waters, m is the quantity of marine water quality control points, $C_i^0$ is background concentration of pollutants at an i-th water quality control point, $C_i^S$ is control target concentration of pollutants at i-th water quality control point, $r_i$ is water quality regulation coefficient of the i-th water quality control point, and $\alpha_{ij}$ is the response coefficient of the unit discharge amount of the j-th pollution source to the pollutant concentration at the i-th water quality control point.

The application has the following beneficial effects.

Firstly, according to the method of the application, the sum of pollutant concentrations at all control points is controlled not to exceed the sum of target concentrations at all single control points, without respectively controlling each control point; a proportion of single control point exceeding the standard is controlled within a range of regulation coefficient according to the characteristics of the control point; after assigning different pollution source discharge coefficients to different pollution source discharge priorities, discharge control amounts of the different pollution sources are determined by solving the objective planning problem of maximizing the virtual total discharge amount.

Secondly, with the method of the application, the problem that each pollution source is generally over-discharged because too many constraints of planning problems lead to low solved allowable total discharge amount is effectively avoided, and the dilemma that the pollutant capacity of the target sea areas is reduced due to the water quality control requirements of individual stations is prevented. Consequently, the method is of great significance for calculating relatively accurate pollutant environmental capacity of the target sea areas.

BRIEF DESCRIPTION OF THE DRAWINGS

In order to explain the embodiments of the present application or the technical scheme in the prior art more clearly, the drawings needed in the embodiments will be briefly introduced below. Obviously, the drawings in the following description are only some embodiments of the present application. For ordinary people in the field, other drawings may be obtained according to these drawings without paying creative labor.

FIG. 1 is a flow chart of an optimal control method of pollutant flux into the coastal waters based on virtual discharge amount in an embodiment of the present application.

DETAILED DESCRIPTION OF THE EMBODIMENTS

In the following, the technical scheme in the embodiment of the application will be clearly and completely described with reference to the attached drawings. Obviously, the described embodiment is only a part of the embodiment of the application, but not the whole embodiment. Based on the embodiments in the present application, all other embodiments obtained by ordinary technicians in the field without creative labor belong to the scope of protection of the present application.

In order to make the above objectives, features and advantages of the present application more obvious and easier to understand, the present application will be further described in detail with the attached drawings and specific embodiments.

The present application provides an optimal control method of pollutant flux into the coastal waters based on virtual discharge amount, as shown in FIG. 1, including: S1, setting water quality control points and water quality targets thereof on the basis of clearly defining a scope of studied sea areas and a list of main pollution sources into the coastal waters; S2, constructing response matrix of coastal water quality to pollution discharged from land by utilizing a numerical model of coastal water quality, extracting response coefficient matrix of different pollution sources and different control points; and S3, establishing a control model for total discharge amount of pollutants into the coastal waters, and calculating optimal allocation amount of pollution load into the coastal waters according to the model.

Specifically, the water quality control objectives in sea areas are set.

the scope of water quality control sea areas and the list of main pollution sources into the coastal waters are defined. A spatial scope of the water quality control sea areas, locations of the main pollution sources into the coastal waters and main categories and sources of pollutants thereof are defined.

On a basis of setting the water quality control objectives in sea areas, the water quality control points in the sea areas are set, where principles of setting the control points is as follows: the water quality target control points are sampling stations used for indicating water quality in the sea areas and quantity and locations the water quality target control points are determined according to the following rule: completeness: selected control points cover marine functional zones contained in all water quality control sea areas, and control point stations are relatively evenly distributed; comparability of data: the selected control points are relatively easy to monitor, and stations with rich historical investigation data are preferably selected; finiteness: representativeness of stations, the expense of monitoring and computation amount of the control model are considered; the control points are controlled within 50 as possible, and 10-30 control points are recommended.

Water quality control objectives are determined. In other words, control objective values of water quality control points are determined. The goals are set mainly based on application types of sea areas where the control points are located. According to functions of different application types and protection goals of sea areas, a water quality control objective of sea areas in marine fishery waters, marine nature reserves and rare and endangered marine life reserves is a first category of seawater water quality criterion;

a water quality control objective of sea areas in aquaculture areas, bathing beaches, marine sports or entertainment areas where human bodies are in direct contact with seawater, and industrial water areas directly related to human consumption is a second category of seawater water quality criterion; a water quality control objective of sea areas in common industrial water consumption areas and coastal scenic tourist areas is a third category of seawater water quality criterion; a water quality control objective of sea areas in marine port waters and marine development operation areas is a fourth category of seawater water quality criterion. The seawater water quality criteria are determined based on technical directives for the division of marine functional zonation (GB 3097-1997).

The response matrix of coastal water quality to pollution discharged from land are constructed by utilizing a numerical model of coastal water quality and response coefficient matrix of different pollution sources and different control points are extracted as follows.

Based on the relationship between pollution sources discharged from land and coastal water quality response concentration, concentration fields formed by individual discharge of each pollution factor of each pollution source item under unit intensity are calculated under an assumption that a concentration model is linear and satisfies a superposition principle. On the basis of determining the location of pollution sources and water quality control points, a two-dimensional water quality model of target sea areas is established by using Mike21 (other marine numerical calculation models may also be adopted) to simulate the influence of different pollution sources discharged into the coastal waters on the water quality of the sea areas.

Parameters of the response coefficient fields for simulation are set as follows.

(1) Convective Diffusion Coefficients

A diffusion coefficient is set as 1 and an attenuation coefficient is set as 0.

(2) Boundary Conditions

Inflow: zero gradient condition

Outflow: radiation condition, $$\frac{\partial C}{\partial t} + U_n \frac{\partial C}{\partial n^w} = 0,$$

where $U_n$ is the normal velocity of the boundary, t is the time, $n^w$ is x or y, and a grid is horizontal;

Shore boundary condition: there is no diffusion, and the normal gradient is 0.

(3) Initial Field a concentration of pollutants at locations of the pollution source items of the response coefficient fields to be extracted is set as 1, and an initial concentration of pollutants in calculated sea areas is set as 0.

(4) Concentration fields formed by a source intensity of point source pollution in the calculated areas of the response coefficient fields is regarded as a linear superposition of concentration fields formed by a source intensity discharge of multiple point source pollutants.

The results of response coefficient fields are set as follows.

The coastal water quality concentration response coefficient field (concentration spatial distribution map of water quality control points) of each pollution source is drawn by unit source intensity to represent spatial characteristics of an impact of each pollution source item into the coastal waters on the water quality of the sea areas.

In this embodiment, the relationship between the source-water quality response concentration of pollutants Chemical Oxygen Demand (COD), inorganic nitrogen and active phosphate is calculated by monthly average in a month with a maximum pollutant discharge amount (for example, August is selected in a case study), and hourly model results of this month are averaged. An average response coefficient table of different pollution sources at each control point is extracted.

The control model for the total discharge amount of pollutants into the coastal waters is established.

Marine environmental capacity is the amount of pollutants that is contained by marine water bodies under the specified environmental targets. Establishing the control model for total discharge amount of pollutants into the coastal waters is regarded as a linear planning problem, and its objective function and constraints are determined to reallocate the environmental capacity in selected pollution source items. Firstly, the response concentration relationship between water quality control points and pollution source terms is established. In other words, the pollution concentration fields $\alpha_{ij}$ (x, y) formed under unit source intensity ($Q_{ij}$=1) is established. According to an actual demand of controlling the total discharge amount of pollutants into the coastal waters, on the one hand, the total discharge amount of pollutants into the coastal waters is required to be maximum as follows:

objective function:

$$\max Q = \sum_{j=1}^{n} \lambda_j Q_j,$$

constraints:
$$\begin{cases} \sum_{i=1}^{m}\left(C_i^0 + \sum_{j=1}^{n}\alpha_{ij}Q_j\right) \leq \sum_{i=1}^{m} C_i^s \\ C_i^0 + \sum_{j=1}^{n}\alpha_{ij}Q_j \leq (1+r_i)C_i^s, i = 1, 2, \dots, m, \\ Q_j \geq Q_{min}^0 \geq 0, j = 1, 2, \dots n \end{cases}$$

where $Q_j$ is the load of the j-th pollution source into the coastal waters; $\lambda_j$ is the regulation coefficient of j-th pollution source, generally $0 \leq \lambda_j \leq 1$; n is the quantity of pollution sources into the coastal waters; m is the quantity of marine water quality control points; $C_i^0$ is the background concentration of pollutants at the water quality control points; $C_i^S$ is control target concentration of pollutants at the water quality control points; $r_i$ is regulation coefficient for water quality objectives; $\alpha_i^j$ is the response coefficient of the unit discharge amount of the j-th pollution source to the pollutant concentration at the i-th water quality control point.

The objective planning problem is solved by substituting a river flow on August of a year along a coast of a certain sea area into a source flow to calculate the pollutant discharge distribution of each source term.

Under the constraints of sea area water quality control, the environmental capacity of Dissolved Inorganic Nitrogen (DIN), Dissolved Inorganic Phosphorus (DIP) and the COD in the sea area is about 384.71 t (ton), 55.56643 t and 18043.88 t respectively.

The above-mentioned embodiment is only a description of the preferred mode of the application, and does not limit the scope of the application. Under the premise of not departing from the design spirit of the application, various modifications and improvements made by ordinary technicians in the field to the technical scheme of the application shall fall within the protection scope determined by the claims of the application.

What is claimed is:

1. A method for optimal control of pollutant flux into waters based on virtual discharge amount, comprising:
    setting water quality control points and water quality control objectives in target sea areas;
    constructing response coefficient fields of coastal water quality to pollution sources discharged from the land, and extracting response coefficient matrix of the different pollution sources and different control points for the water quality control points through the response coefficient fields of coastal water quality to pollution sources discharged from the land; and
    establishing a control model for a total discharge amount of pollutants into waters through the response coefficient matrix and calculating an optimal control amount of flux of the different pollution sources into the waters based on the control model for the total discharge amount of pollutants into the waters;
    wherein constructing response coefficient fields of coastal water quality to pollution sources discharged from the land comprises:
    calculating steady-state concentration fields formed by individual discharge of each pollution factor of each pollution source item under unit intensity respectively based on a relationship between response concentration of coastal water quality and pollution sources discharged from the land, and establishing a two-dimensional water quality model of the target sea areas based on pollution source positions and the water quality control points; simulating and studying effects of the different pollution sources discharged into the waters on the water quality of the sea areas based on the two-dimensional water quality model of the target sea areas, and obtaining the response coefficient fields of coastal water quality to pollution sources discharged from the land corresponding to the different pollution sources;
    parameters of the response coefficient fields of coastal water quality to pollution sources discharged from the land comprise:
    convective diffusion coefficients and boundary conditions, wherein the convective diffusion coefficients comprise a diffusion coefficient, an attenuation coefficient and an initial concentration, and the boundary conditions comprise open boundary conditions, inflow, outflow and shore boundary conditions;
    establishing the control model for the total discharge amount of pollutants into the waters comprises:
    a sum of actual pollutant concentrations at all water quality control points does not exceed a sum of target concentrations thereof, and a proportion of water quality exceeding a standard at each control point does not exceed a water quality regulation coefficient at that point, with a goal of maximizing the virtual total discharge amount in the sea areas, the total discharge amount control model of the pollutants is constructed by solving an optimal solution of an objective planning model;
    an objective function of the control model for the total discharge amount of pollutants into the waters is:

$$\max Q = \sum_{j=1}^{n} \lambda_j Q_j,$$

wherein $Q_j$ is a load of a j-th pollution source into the waters, $\lambda_j(\lambda_j \geq 1)$ is a regulation coefficient of the j-th pollution source, Q is the virtual total discharge amount and n is a quantity of pollution sources discharged from the land into the waters; and constraints of the control model for the total discharge amount of pollutants into the waters comprise:

$$\begin{cases} \sum_{i=1}^{m}\left(C_i^0 + \sum_{j=1}^{n}\alpha_{ij}Q_j\right) \leq \sum_{i=1}^{m}C_i^s \\ C_i^0 + \sum_{j=1}^{n}\alpha_{ij}Q_j \leq (1+r_i)C_i^s, i = 1, 2, \ldots, m, \\ Q_j \geq Q_{min}^0 \geq 0, j = 1, 2, \ldots n \end{cases}$$

wherein n is a quantity of pollution sources discharged from the land into the waters, m is a quantity of marine water quality control points, $C_i^0$ is a background concentration of pollutants at an i-th water quality control point, $C_i^S$ is a control target concentration of pollutants at i-th water quality control point, $r_i$ is a water quality regulation coefficient of the i-th water quality control point, and $\alpha_{ij}$ is a response coefficient of the unit discharge amount of the j-th pollution source to the pollutant concentration at the i-th water quality control point.

2. The method for optimal control of pollutant flux into waters based on virtual discharge amount according to claim 1, wherein principles of setting the water quality control points in the target sea areas comprise completeness, comparability of data and finiteness, wherein the completeness means selected control points cover marine functional zone types contained in all water quality control sea areas, and control point stations are evenly distributed; the comparability of data means stations with rich historical investigation data are preferably selected to be used for comparative research; and the finiteness is to consider a representativeness of the stations, expense of monitoring and investigation and a computation amount of the control model at a same time.

3. The method for optimal control of pollutant flux into waters based on virtual discharge amount according to claim 2, wherein a basis of setting the water quality control objectives is set according to application types of the sea areas of the water quality control points.

4. The method for optimal control of pollutant flux into waters based on virtual discharge amount according to claim 3, wherein the application types of the sea areas comprise:
    a water quality control objective of sea areas in marine fishery waters, marine nature reserves and rare and endangered marine life reserves;

a water quality control objective of sea areas in aquaculture areas, bathing beaches, marine sports or entertainment areas with human bodies in direct contact with seawater, and industrial water areas directly related to human consumption;

a water quality control objective of sea areas in industrial water consumption areas and coastal scenic tourist areas; and a water quality control objective of sea areas in marine port waters and marine development operation areas.

\* \* \* \* \*